United States Patent [19]

Gaffar

[11] Patent Number: 5,472,685

[45] Date of Patent: Dec. 5, 1995

US005472685A

[54] ANTIPLAQUE ORAL COMPOSITIONS

[75] Inventor: Abdul Gaffar, Princeton, N.J.

[73] Assignee: Colgate Palmolive Company, Piscataway, N.J.

[21] Appl. No.: 265,987

[22] Filed: Jun. 27, 1994

Related U.S. Application Data

[63] Continuation of Ser. No. 648,504, Jan. 30, 1991, Pat. No. 5,356,615.

[51] Int. Cl.$^6$ ............................. A61K 7/16; A61K 7/24; A61K 7/26
[52] U.S. Cl. ............................. 424/49; 424/55; 424/58; 514/901
[58] Field of Search ................... 424/49, 55, 58

[56] References Cited

U.S. PATENT DOCUMENTS 5,256,396  10/1993  Piechota, Jr. .............................. 424/49

Primary Examiner—Thurman K. Page
Assistant Examiner—James M. Spear
Attorney, Agent, or Firm—Robert C. Sullivan; Robert L. Stone; Murray M. Grill

[57] ABSTRACT

An antiplaque oral composition, such as a toothpaste, gel dentifrice, tooth powder, mouthrinse or mouthwash, tooth hardener, anticalculus composition, gum or lozenge, comprises triclosan as an antiplaque component, the antiplaque action of which is unexpectedly and beneficially increased by the presence in the oral composition of a phenolic flavoring agent, such as eucalpytol, thymol, methyl salicylate, menthol, phenol, halogenated derivatives thereof, and mixtures thereof. Preferred such compositions are toothpastes, gel dentifrices and mouthrinses or mouthwashes. Also within the invention are processes of repeatedly applying such antiplaque oral compositions to the teeth to obtain the antiplaque benefits mentioned.

15 Claims, No Drawings

ANTIPLAQUE ORAL COMPOSITIONS

This is a continuation of application Ser. No. 07/648,504, filed Jan. 30, 1991, now U.S. Pat. No. 5,356,615, issued Oct. 18, 1994.

This invention relates to antiplaque oral compositions. More particularly, it relates to such compositions which contain triclosan, as an antiplaque component, with a phenolic compound which unexpectedly increases the antiplaque activity of the triclosan and also acts as a flavoring agent for the composition.

Various oral compositions, such as toothpastes and mouthrinses, which have been manufactured and sold, have included in their formulas components intended to promote dental health, in addition to components intended primarily to clean teeth and sweeten breath. For examples, triclosan has been included in both toothpaste and mouthrinse formulations for its antiplaque action and flavoring agents present in toothpastes and mouthrinses have included phenolic compounds. Additionally, various other materials have been included in such oral composition formulations for their desired properties, among which are polishing agents, thickening agents, surfactants, humectants, solvents, sweeteners, tooth hardeners, antitartar agents, anticalculus agents and antibacterial agents.

Although the art was aware of the utilities of triclosan as an antiplaque agent and of phenolic materials as flavoring agent in oral compositions aplicant does not know of any disclosure or suggestion in the art of both triclosan and phenolic flavoring agents being present in the same oral composition and does not know of any disclosure(s) which describe(s) or suggest(s) that the antiplaque activity of triclosan would be greatly improved by the presence of phenolic flavoring agent. Thus, the oral compositions of this invention are novel and unobvious from the art.

Applicant is aware of and calls attention to the following art of interest:

Triclosan is described in U.S. Pat. No. 4,022,880, 4,749,562 and 4,894,220, German OLS 3532860 and European Patent Applicants Nos. 0161898, 0161899 and 0220890. In such references it is disclosed as an antibacterial agent in mouthrinses and dentifrices, sometimes with zinc and copper compounds. Triclosan is also disclosed as a component of oral compositions in U.S. patent applications Ser. Nos. 07/505,628, now U.S. Pat. No. 5,167,957, 07/547,641, now U.S. Pat. No. 5,260,062 and 07/547,642, now U.S. Pat. No. 5,234,688. Phenolic flavoring agents have been employed to flavor oral compositions and some of them have been included in such compositions for their antibacterial properties.

While triclosan alone in oral compositions, even in relatively small proportions, can noticeably decrease plaque formation when such compositions are applied to the teeth, and while phenolic flavoring agents, in addition to flavoring such compositions, can also act to decrease plaque formation on the teeth, the reduction in plaque formation when both are employed in the same oral composition is surprisingly better than would have been expected, often being more than 20% more than that which would have been reasonably expected from the additive activities of the triclosan and the flavoring agent. Because plaque formation is often associated with gingivitis the invented oral compositions are also useful for preventing the development of such condition.

In accordance with the present invention an antiplaque oral composition comprises an orally acceptable vehicle or base for such composition, an effective antiplaque proportion of triclosan and a phenolic flavor for the oral composition in a proportion which significantly increases the antiplaque action of the triclosan on the teeth of a user of the oral composition.

Triclosan, which has been described in the reference patents and applications previously mentioned, is known as an effective compound for inhibiting growths of microorganisms, especially bacteria. Because bacteria are components of plaque, triclosan reduces plaque formation when it is effectively applied to the teeth Triclosan is of the formula 2',4,4'-trichloro-2-hydroxy-diphenyl ether, and is the highly preferred antiplaque agent of this invention. However, other noncationic diphenyl ethers may be employed in replacement of it (partial replacement is preferable), such as 2,2'-dihydroxy- 5,5'-dibromo-diphenyl ether and other halogenated and hydroxy-substituted diphenyl ethers of similar types. Such compounds are preferred antibacterial agents in oral compositions because, unlike cationic antibacterial compounds, they do not stain the teeth and are not of unacceptable flavors.

"Phenolic flavors" as that term is employed in this specification, describes those compounds which include phenolic groups, or derivatives thereof, which are orally acceptable and which have an acceptable flavor, which is preferably like that of the preferred flavors of the working example formulas that will be given subsequently in this specification.

Such flavors are selected from the group consisting of eucalyptol, thymol, methyl salicylate, menthol, chlorothymol and phenol, and halogenated and other derivatives thereof, with the first six being more preferred, and the first four being even more preferred. Although any of such phenolic flavors may be employed alone it may normally be preferred to utilize mixtures of two or more thereof and preferably all four (of the first four listed) will be in the final flavor composition. In such composition it is desirable that there be at least about 5% of each of such four flavors in the total flavor, preferably at least about 10%, and more preferably at least about 15% of each. A much preferred composition includes about 35% of eucalyptol, about 27% of thymol, about 21% of methyl salicylate and about 17% of menthol.

The antiplaque oral compositions of this invention are preferably mouthwashes or mouthrinses, or dentifrices, such as toothpastes and gels, but various other such compositions may also be given the described improved antiplaque properties by including in them triclosan and a phenolic flavor. Such compositions include tooth powders, tooth hardeners (usually of the professionally applied type), antitartar compositions, anticalculus compositions, gums, tablets and lozenges. For liquid state compositions of the invention, such as mouthrinses, mouthwashes, tooth hardeners and antiplaque and antitartar compositions the liquid medium in which the active components are present will normally be aqueous and often will be aqueous alcoholic, with ethanol being the preferred alcohol. Such compositions often also contain a humectant, such as a polyol, e.g., glycerol, sorbitol, mannitol, polyethylene glycol, propylene glycol, or a mixture of two or more thereof, and a surfactant, such as a dental detergent or a mixture of such detergents. Other adjuvants and active components may also be present and such will be described later.

For the paste, gel, solid and particulate solid state compositions of the invention, such as toothpastes, gel dentifrices, tooth powders, chewing gums, tablets and lozenges, the base or the medium for the active components will usually be any which is employed in such compositions that do not contain the combination of triclosan and phenolic flavoring agent. For the toothpaste and gel dentifrices such bases will usually comprise: water; humectant; polishing agent, such as finely divided silica, calcium carbonate, tricalcium phosphate, dicalcium phosphate and/or insoluble sodium metaphosphate (of which the finely divided silica polishing agent is preferred); and a surfactant, such as sodium lauryl sulfate, sodium N-coco, N-methyl taurate, sodium N-lauroyl sarcosine, or other compatible dental detergent. A thickener, which will preferably be a natural or synthetic gum, such as carrageenan or hydroxymethyl cellulose, or a siliceous thickener such as fumed silica, or a mixture of such thickeners will also often be employed to help to increase paste or gel viscosity or body and it can function as a gelating agent. Other known thickeners and gelating agents may be employed in place of those specifically mentioned above and other known polishing agents, humectants and surfactants may also be used. Bases for tooth powders will normally be almost entirely of polishing agent, with some surfactant desirably being present. The base for the gum can be an elastomer of a type normally employed in chewing gums, e.g., chicle, gum or rubber, and the tablets and lozenges may have a hard sugar or candy base but preferably will be of sorbitol or a gummy material, such as gelatin.

The various oral compositions of the invention may contain adjuvants and additional active components to make them more acceptable to the consumer and to make them more effective in use. Because the compositions are intended for oral uses they will often be sweetened with saccharin or aspartame and will be flavored. Although the preferred flavors are the phenolic flavors, as was previously mentioned, it is within the invention to utilize non-phenolic flavors in addition to the phenolic flavors (not in replacements thereof). Coloring agents may be employed, as may be speckles or other visual adjuvants, and in cases where undesirable reactions could occur between components during storage before use, some of such reactants may be separated from others by being incorporated in such speckles or by being packed in dispensing containers having separate sections to prevent such reactions.

Among the active materials which may be included in the compositions there may be mentioned azacycloalkane diphosphonic compounds, such as azacycloheptane diphosphonic acid and salts thereof, which have an anticalculus effect. Such are described in U.S. patent application Ser. No. 07,631,232, of Gaffar, Afflitto and Joziak, entitled Anticalculus Oral Compositions, which was filed on Dec. 20, 1990, now U.S. Pat. No. 5,096,699. Synthetic anionic polymeric polycarboxylates, such as copolymers of maleic acid or maleic anhydride with vinyl methyl ether, and their salts, e.g., sodium salts, which are sold under the trademark. Gantrez®, improve the anticalculus action of the mentioned diphosphonic compounds and also have stabilizing and other desirable effects on other active materials, such as polyphosphates, e.g., sodium pyrophosphate, which can be employed as antitartar agents. Fluorides and other sources of fluoride ions, such as sodium fluoride and sodium monofluorophosphate, are also active components which may be utilized, for their tooth hardening effects. Various adjuvants and active components mentioned above are described further in the patents, publications and applications cited herein, which are hereby incorporated herein by reference. More detailed descriptions of some such components are given subsequently in this specification.

A source of fluoride ions may be water soluble or relatively water insoluble, so long as it releases a sufficient quantity of such ions during use. Among the useful sources of fluoride ions are: soluble alkali metal fluorides, such as sodium and potassium fluorides; copper fluorides, such as cuprous fluoride; tin fluorides, such as stannous fluoride; ammonium fluorosilicate; sodium fluorozirconate; ammonium fluorozirconate; sodium monofluorophosphate; aluminum fluorophosphates (mono-, di- and tri-); and fluorinated sodium calcium pyrophosphate. Of these, alkali metal and tin fluorides, such as sodium and stannous fluorides, sodium monofluorophosphate (MFP®) and mixtures thereof, are preferred.

Polyphosphate anti-tartar agents may include any of various suitable polyphosphates, such as alkali metal tripolyphosphates and pyrophosphates, but sodium pyrophosphate is preferred.

The synthetic anionic polymeric polycarboxylates (SAPP's), which stabilize the polyphosphates and improve the present antiplaque oral compositions too, may be of molecular weights in the range of about 5,000–2,000,000, preferably about 50,000–1,500,000 and more preferably 500,000–1,000,000, e.g., about 1,000,000, and are available from GAF Corporation under the designations Gantrezes® AN-169, AN-139, AN-119 and S-97, pharmaceutical grade. Such SAPP's are all linear copolymers but cross-linked polymers, such as those sold under the trade mark Carbopol®, of B. F. Goodrich, e.g., Carbopols 934, 940 and 941, may be substituted, preferably only in part. Corresponding analogues of the SAPP's may also be substituted, in whole or in part, including known polysulfonates, polysulfates and polyphosphonates. Other olefinic monomers that are copolymerizable with the described acids or anhydrides include vinyl acetates, vinyl chloride, dimethyl maleate and similar unsaturated monomers, and the copolymers made will contain a sufficient proportion of acidic groups or neutralized or neutralizable acidic groups to make them water soluble or swellable. Some such polycarboxylate copolymers are those disclosed in U.S. Pat. Nos. 4,138,477 and 4,183,914, and include copolymers of maleic anhydride with styrene, isobutylene or vinyl ethyl ether, polyacrylic, polyitaconic and polymaleic acids, and sulfoacrylic oligomers of comparatively low molecular weights, such as Uniroyal® ND-2.

The water employed in the present compositions may be city water and the hardness thereof may be as high as 300 or even 500 p.p.m., as calcium carbonate, in some instances, but it will be preferred to limit the hardness to no more than 100 or 150 p.p.m., and it will be more preferred to employ zero hardness water or deionized water, which is most preferably irradiated before being compounded with the other components of the oral compositions. Among additional adjuvants that may be included in the invented compositions are buffers and neutralizing agents to control pH, bleaching agents and tooth whiteners, preservatives, dyes and pigments. Also, various other non-interfering or substantially non-interfering adjuvants of types generally useful in oral compositions like those of this invention may be included.

The proportions of the required components of the invented compositions will often be in certain ranges to obtain the antiplaque effects desired. The proportion of triclosan to phenolic flavor will normally be within the range of about 5:1–1:100, preferably being in the range of about 2:1–1:20 and more preferably in the range of about 3:2–1:10. Percentages of triclosan and phenolic flavor in the compositions will normally be within the ranges of about 0.01–1% and about 0.02–2%, respectively, preferably about 0.01–0.5% and about 0.05–1.5%, respectively, and more preferably about 0.03–0.4% and about 0.05–1%, respectively.

In antiplaque oral compositions which are in the form of a toothpaste, gel dentifrice or tooth powder (wherein contents of active components are normally greater than for the mouthrinses) and also in the gums, tablets, lozenges and professionally applied treatments the percentages of required components may be about 0.1–1% triclosan and about 0.5–2% of phenolic flavors, preferably about 0.1–0.5% and about 0.5–1.5%, respectively, and more preferably about 0.2–0.4% and about 0.7–1.2%, respectively. In such compositions the contents of each of eucalpytol, thymol, methyl salicylate and menthol, which are the preferred components of the phenolic flavor, are at least about 0.05%, preferably at least about 0.1% and more preferably at least about 0.15% (with the 0.15% contents requiring at least 0.6% of total phenolic flavor). It is appreciated that methyl salicylate and phenol are toxic to humans in amounts considerably greater than those likely to be ingested by users of the invented compositions but when the invented oral preparations are to be used by unsupervised children contents of methyl saliculate and phenol and of any other toxic phenolic flavors will normally be reduced to such levels, e.g., less than 0.4% total, or may be omitted, so as to prevent any adverse effects, even if entire packages of the compositions were to be ingested by a child. Toothpastes and gel dentifrices also will normally contain about 10–40% of dental polishing agent, preferably about 15–25% of finely divided silica, about 15–45% of humectant, preferably about 20–40%, about 0.5–8% of thickener, preferably about 2–6% of gum and/or silica thickener(s), about 0.2–5% of surfactant, preferably about 0.5–3% of dental detergent, (which is normally an anionic or amphoteric detergent or a mixture thereof), about 20–70% of water, preferably about 35–55%, and, if SAPP is to be present, about 0.5–5% thereof of a molecular weight of about 5,000–2,000,000, preferably about 1–3% of a sodium salt of a linear copolymer of maleic anhydride or maleic acid with vinyl methyl ether, which is of a molecular weight in the range of about 50,000–1,500,000.

In the antiplaque oral compositions which are mouthrinses or mouthwashes, or which are in liquid form and are intended for application to the teeth by the consumer, rather than by a professional, lesser proportions of active components will often be present, percentages of triclosan and phenolic flavor(s) will often be within the ranges of about 0.01–0.2% of triclosan and about 0.02–1% of phenolic flavor, preferably about 0.01–0.1% and about 0.02–0.5%, respectively with the phenolic group being selected from the group consisting of eucalyptol, thymol, methyl salicylate and menthol, and mixtures thereof. More preferably such percentages will be about 0.03–0.06% and about 0.05–0.25%, respectively, and the phenolic flavoring will include at least 10% of each of eucalyptol, thymol, methyl salicylate and menthol. In the more preferred mouthrinses or mouthwashes there will also be present about 5–20% of ethanol, about 10–50% of humectant and up to about 85% of water, with the water being the balance of the composition, after allowances for the presences of other active components and optional adjuvants, which may also be present. In still more preferred antiplaque mouthwashes of the invention the percentage of triclosan will be in the range of about 0.03–0.06%, that of phenolic flavor will be in the range of about 0.05–0.25% and the phenolic flavor will include at least about 15% thereof of each of eucalyptol, thymol, methyl salicylate and menthol, the humectant will include about 1–20% of each of glycerol and propylene glycol and about 1–25% of sorbitol, about 5–20% of ethanol and about 0.05–1% of dental surfactant will be present, as will be about 0.05–1% of a linear copolymer of maleic anhydride or maleic acid with vinyl methyl ether, which is of a molecular weight in the range of about 50,000–1,500,000, and the water content of the composition, except for any additional adjuvants and active components present, will be in the range of about 27.69–84.82% of water. The total of additional adjuvants in the composition will normally be minimized, usually being held to a maximum of a 10% and preferably being in the range of 0.1–5%, and replacing water.

In addition to the invented antiplaque compositions, also within the present invention is a process for treating teeth to inhibit plaque development on them, which comprises applying to the teeth a plaque inhibiting amount of the composition of this invention. Although some antiplaque action may be detectable after a single treatment of the teeth with an invented composition, for effective antiplaque action such composition(s) should be applied repeatedly, preferably being employed at least once a day for at least four (and preferably seven) consecutive days and more preferably at least twice a day for at least seven or ten consecutive days. Such application rates are for toothpastes, gel dentifrices and toothpowders. It has been found that uses of the invented mouthrinses or mouthwashes at the rate of once a day will measurably diminish plaque development even when employed for only four consecutive days. However, as with the dentifrices, it is preferred to utilize the mouthwash at least twice a day (and preferably more) for at least seven consecutive days. In the above descriptions of the processes of the invention it is to be understood that variations in the procedure, whereby a day or two is missed, are still within the invention providing that the number of days of application is as specified.

The described toothpastes and gel dentifrices may be packaged in conventional metal or plastic "squeeze tubes", in piston actuated dispensers, in pressurized "aerosol" dispensers or in other suitable containers, which are preferably of the dispensing type. If the container for the dentifrice (or mouthrinse) is plastic it will be preferable to include limonene or other such stabilizing terpene in the flavor or as an adjuvant to stabilize the triclosan against any possible decomposition due to contact with such plastic under elevated temperature storage conditions. The stabilizing effect on triclosan of limonene and other terpenes vs. reactive plastics is described in the aforementioned U.S. patent application Ser. No. 07/505,628, U.S. Pat. No. 5,167,951 and normally the percentage employed will be in the range of about 0.01–2%, preferably about 0.1–0.5%. Like the phenolic flavoring agent the terpene(s) may be present as a part of the total flavor composition. Employment of the stabilizing agent will not be necessary when the plastic employed is inactive toward triclosan but it may often be advisable to include the terpene stabilizer in the oral composition and dentifrice formulas as a safety measure.

Manufacturing of the dentifrices of this invention is comparatively simple because, in general, there is little or no criticality in the orders of additions of the various components present in such compositions. Initially one forms a pre-mix of most or all of the water, in which the surfactant has been dissolved, and then triclosan is admixed with that, followed by other water soluble components and the water insoluble components, if any. If desired, the lipophilic components may be pre-mixed together and such pre-mix may be mixed with the hydrophiles pre-mix, after which the water insoluble particulate materials may be blended in, as in the cases of toothpastes and gels. Such procedures are typical of those employed in manufacturing dentifrices, with the only exception being in the preferred addition of triclosan to the water solution of surfactant as an initial production step.

Manufacture of the mouthrinses or mouthwashes is even simpler because in such case the ethanol and water are mixed and the other components (which are almost always soluble in the aqueous alcoholic medium) are then admixed with it, with the surfactant and triclosan preferably being admixed first with such medium. The toothpowder may be made by merely blending the various powdered components thereof and the professional tooth hardening preparations and antiplaque compositions may be made by substantially following the procedure described for manufacturing the mouthrinses. Making the gums and lozenges may be by procedures normally employed in manufacturing such products, with the active components usually preferably being added near the end of the manufacturing process if heat is employed, so as to minimize subjection of such materials to elevated temperatures. All the processes for manufacturing the invented compositions may be carried out at room temperature, as a rule, except for those usually employed for manufacturing the gums and lozenges, and in such cases heating may be desirably minimized to the extent that such is practicable. Employing the invented compositions is easy and processes for inhibiting formation of plaque on the teeth normally merely involve using such preparations in normal manners. Thus, the teeth are brushed with the toothpaste or dentifrice gel, the mouth is rinsed with the mouthrinse or mouthwash, the tooth hardener and other liquid dental preparations are applied to the teeth from swabs or by rinsing the mouth with them, the gum is chewed, and the tablets and lozenges are allowed to dissolve slowly in the saliva in the mouth. In all such cases uses of the invented compositions (or of their separate active components) will cause a decrease in plaque development on the teeth, so the teeth will be cleaner, whiter, brighter and of better appearance. When whitening or bleaching agents are present in the oral compositions, such as peroxides or other per-compounds the teeth will be made still whiter, due to bleachings of food stains and any other bleachable stains that are on them.

Improvements in tooth surfaces, as mentioned above, are noticeable visually, and especially instrumentally and diognostically, after several or more treatments with the invented compositions, and for best effects the compositions should be employed on a regular daily basis, at least once a day and preferably twice, for a period of at least four days, preferably seven or ten, and more preferably for at least a month. Ideally, such treatments should be ongoing, even for years, just as conventional toothbrushings and uses of mouthrinses are daily or twice daily routine functions for those who concientiously care for their teeth. From such continued regular use the desirable antiplaque and tooth hardening effects of the fluoride-containing products of the invention will be obtained (and such results will be improved further when special professional applications of such invented compositions are made).

The following examples illustrate the invention but do not limit it. Unless otherwise mentioned all parts and percentages in this specification, these examples and the appended claims are by weight and all temperatures are in °C.

EXAMPLE 1

| | (Mouthrinse) | | | |
|---|---|---|---|---|
| | Percent (by weight) | | | |
| Component | A | B | C | D |
| Triclosan | 0.06 | 0.06 | — | — |
| (1) Phenolic flavor | 0.25 | — | 0.25 | — |
| (2) Gantrez S-97, pharmaceutical grade (100% active polymer basis) | 0.25 | 0.25 | 0.25 | 0.25 |
| (3) Tauranol WS | 0.25 | 0.25 | 0.25 | 0.25 |
| Sodium lauryl sulfate | 0.2 | 0.2 | 0.2 | 0.2 |
| Ethanol | 10.0 | 10.0 | 10.0 | 10.0 |
| Sorbitol solution (70% aqueous) | 20.0 | 20.0 | 20.0 | 20.0 |
| Glycerol | 10.0 | 10.0 | 10.0 | 10.0 |
| Propylene glycol | 7.0 | 7.0 | 7.0 | 7.0 |
| Water | 51.99 | 52.24 | 52.05 | 52.30 |
| | 100.00 | 100.00 | 100.00 | 100.00 |

Each mouthrise is made by first mixing together, at room temperature, the ethanol and water, after which there are admixed with such aqueous alcoholic medium the surfactants, triclosan, flavor, humectants and copolymer that are in the formulas. The finished mouthrinses may be filtered but normally that is unnecessary.

The mouthrinses made were evaluated for their abilities to arrest plaque growth during a four-day period of use by ten human test subjects. The subjects employed were in the age group of 26–40 years, had an average of 27 teeth and had no clinical or radiographical signs of caries lesions or periodontal tissue breakdown. To create conditions favorable for the development of plaque participants in the tests did not brush the teeth or practice any other mechanical oral hygiene during the test. At the beginning of the test all ten subjects were given professional tooth cleanings to remove any existing plaque deposits. During the various tests they did not brush their teeth but did rinse their mouths with one of the four mouth rinses during different test periods, so that each mouthrinse formula was tested by the ten subjects. Rinsings were twice a day, in the morning and in late afternoon, and were performed in a supervised setting and in a standardized manner. Ten milliliters of mouthwash were employed for a thirty second rinse on each rinsing occasion. After four days of use examinations were made of the subject's teeth, with the plaque being made visible by application to it of a disclosing dye, manufactured by Diaplaque Co., of Astra, Sweden. The Silness and Loe method was employed and statistical analyses were made by analyses of variances, followed by Student—Neuman Keul's test. Results of these tests are given in Table 1, which follows:

TABLE 1

| Test | Plaque Index | Reduction in Plaque (%) (4) |
|---|---|---|
| A (triclosan + flavor) | 0.30 | 81 |
| B (triclosan) | 0.78 | 51 |
| C (flavor) | 0.96 | 40 |
| D — | 1.60 | — |

(4) Percentages of plaque reduction are given with respect to the control, D.

From the data presented in Table 1, it is clear that when triclosan and phenolic favor are employed in an oral composition, such as a mouthrinse, plaque development is significantly reduced, compared to such reduction by the uses of mouthrinses containing either triclosan or phenolic flavor only. Furthermore, the addition of the phenolic flavor to the B formula (to make the A formula) reduces the plaque index for the B formula by about 62% (from 0.78 to 0.30), which is more than the 40§ that is shown for the reduction by the flavor alone, as is seen by comparison of the plaque indices for Formulas C and D. Also, such a reduction in plaque is more significant than a reduction of a similar percentage would be from a control wherein plaque development is normally greater, because it is normally considered to be more difficult to reduce an already reduced level of plaque than it is to reduce a higher level.

Similar plaque reduction results are attainable when the percentages of triclosan and flavor are varied over the ranges previously given herein, e.g., about 0.06 and 0.15%, respectively.

EXAMPLE 2

(Toothpaste)

| Component | Percent (by weight) |
|---|---|
| Triclosan | 0.30 |
| (1) Phenolic flavor | 0.95 |
| (2) Gantrez S-97, pharmacuetical grade (100% active polymer basis) | 2.00 |
| Sodium lauryl sulfate | 1.50 |
| (5) Zeodent 113 | 20.0 |
| (6) Sylodent 15 | 3.0 |
| Iota carageenan (thickener) | 0.75 |
| Sorbitol | 21.0 |
| Propylene glycol | 10.0 |
| Sodium hydroxide | 0.80 |
| Titanium dioxide | 0.50 |
| Sodium saccharin | 0.40 |
| Water | 38.8 |
| | 100.00 |

(5) Finely divided silica polishing agent
(6) Silica thickener

This toothpaste composition is made in the normal manner described previously in the specification, with the triclosan being mixed with a pre-mix of the sodium lauryl sulfate and water, after which the humectant, thickeners, polishing agent, neutralizing agent, sweetener and flavor are admixed. The product resulting is like a conventional toothpaste in appearance and physical characteristics but when employed regularly in the brushing of the teeth, for example once a day for seven or ten days or twice a day for similar periods of time or longer, it significantly reduces plaque development on the teeth. If either or both of the triclosan and phenolic flavor is/are omitted from the formula the antiplaque action of the toothpaste is significantly diminished.

EXAMPLE 3

(Tooth Powder)

| Component | Percent (by weight) |
|---|---|
| Triclosan | 0.30 |
| (1) Phenolic flavor | 1.0 |
| (7) Gantrez AN-169 | 1.5 |
| Sodium lauryl sulfate | 0.5 |
| (5) Zeodent 113 | 96.7 |
| | 100.00 |

(7) Copolymer of maleic acid or anhydride with vinyl methyl ether, mfd. by GAF Corporation and reported by GAF to be of a molecular weight of about 750,000 (vapor pressure osmometry)

A tooth powder of the above formula is made by mixing together the indicated components in a suitable powder mixer, such as a V-blender. In an anticalculus, antiplaque tooth powder there will also be present 1% of azacycloheptane-2,2-diphosphonic acid as an anticalculus agent, and the anticalculus activity will be improved due to the presence of the Gantrez. Also, 0.2–0.3% of sodium fluoride may be present for tooth hardening. In a preferred formula there is also present about 0.1–1% of other flavoring agents, including a terpene flavor, such as a limonene, and other flavors, including peppermint and spearmint, may also be a part of the total flavor.

The tooth powder produced is an excellent cleaner for the teeth and protects them against development of plaque thereon, which helps to prevent gingivitis. Cosmetically, the antiplaque tooth powder helps to keep the teeth clean after brushing, preventing dulling of the surfaces thereof, which can be caused by the formation of plaque on them. Use of the tooth powder should be regular, at least twice daily, for at least a month, and preferably for life, but a toothpaste may be substituted.

EXAMPLE 4

(Lozenge or Tablet)

| Component | Percent (by weight) |
|---|---|
| Triclosan | 0.30 |
| (1) Phenolic flavor | 1.0 |
| (2) Gantrez S-97, pharmaceutical grade | 0.3 |
| Sorbitol | 96.7 |
| Sodium saccharin | 0.20 |
| Magnesium stearate | 0.50 |
| Polysorbate 20 (emulsifier) | 1.0 |
| | 100.00 |

Lozenges of the above formula may be made by melting the sorbitol and dissolving/dispersing the other components in it, after which the mix is allowed to solidify at room temperature. Alternatively, tablets may be made by mixing together the powdered components and pressing the mix in a tablet press. The lozenges and tablets so made are effective in combatting formation of plaque on teeth when used at least once a day for a month but preferably they are used twice daily for two or more months or longer, and the antiplaque results will be even better.

Instead of employing sorbitol as a base other sugars and sugar alcohols may be substituted for it in whole or in part, e.g., mannitol, sucrose and glucose, or mixtures thereof, and similar results are obtainable. Alternatively, gums and gelatins may be the bases for such lozenges, candies or tablets, and the proportions of the active components may be increased, to as much as 2% of the phenolic flavoring agent and to as much as 1% of triclosan.

EXAMPLE 5

(Chewing Gum)

| Component | Percent (by weight) |
|---|---|
| Triclosan | 0.3 |
| (1) Phenolic flavor | 0.95 |
| (8) Gantrez AN-119 | 0.25 |
| Sorbitol/mannitol mixture (50:50) | 35.0 |
| Sodium saccharin | 0.03 |
| Chicle base | 20.0 |
| Starch (binder) | 10.0 |
| Talc (filler) | 33.47 |
| | 100.0 |

(8) Copolymer of maleic acid or anhydride with vinyl methyl ether, mfd. by GAF Corporation and reported by GAF to be of a molecular weight of about 250,000 (vapor pressure osmometry)

A chewing gum of the above formula is made by blending together the formula components in a suitable mixer, such as a Banbury mixer. Such a chewing gum is effective in inhibiting the development of plaque on the teeth when chewed daily, preferably several times daily, for at least seven to ten days. It is also effective when the proportion of the active components, the triclosan and phenolic flavor, are changed ±10, 20 and 30%, while still remaining within the ranges previously given in this specification. For best antiplaque effects the gum should be chewed several times daily for one or more minutes at a time for at least a month.

In the working examples the described products, the formulas of which have been given above, may be modified by replacement of active and supplementary components with others that were previously named and referred to herein, and the proportions thereof may be changed, e.g., ±10, 20 or 30% within the ranges recited herein, and effective antiplaque compositions result. A terpene stabilizer, e.g., limonene, for triclosan may also be utilized, and may often be in the range of 0.05–0.5% of the composition. Triclosan may be replaced, preferably only in part, e.g., 5 to 49%, by 2,2'-dihydroxy-5,5'-dibromo-diphenyl ether and other brominated, chlorinated and hydroxy-substituted diphenyl ethers of similar types, which also have antiplaque properties. The other disclosed Gantrezes may be substituted for the Gantrezes recited in the examples, at least in part, and the other mentioned surfactants may be employed in place of sodium lauryl sulfate and sodium N-methyl N-coco taurate. It will be desirable to keep the content of sodium lauryl sulfate no higher than about 0.2% in mouthwash compositions, because of adverse effects on the flavor of greater proportions thereof. In the toothpastes one may substitute for the silica polishing agents other polishing agents, including calcium carbonate, insoluble sodium metaphosphate, tri- and di-calcium phosphates. Polyphosphates may be present as antitartar agents. Sources of fluoride ion, such as sodium monofluorophosphate (MFP®) and sodium fluoride, may also be present. Sodium saccharin may be replaced as a sweetening agent by aspartame. Compositions of the changed example formulas will all be effectively antiplaque when employed in the manners described in these examples and in the specification.

The invention has been described herein with references to working examples and specific embodiments thereof but is not to be limited to these because one of skill in the art with the present specification before him or her will be able to utilize substitutes and equivalents without departing from the invention.

What is claimed is:

1. An antiplaque oral composition which comprises an orally acceptable vehicle or base for such composition, an effective antiplaque proportion of triclosan and phenolic flavor for the oral composition in a proportion which significantly increases the antiplaque action of the triclosan on the teeth of a user of the oral composition, wherein the composition is a toothpaste, gel dentifrice, tooth powder, mouthrinse, mouthwash, tooth hardener, anticalculus composition, gum or lozenge, the phenolic flavor consists essentially of eucalyptol, thymol, methyl salicylate and menthol, the proportion of triclosan to such phenolic flavor therein is in the range of about 5:1–1:100 and the percentages of triclosan and such phenolic flavor in the composition are in the ranges of about 0.01 to 1% and about 0.02 to 2%, respectively.

2. An antiplaque oral composition according to claim 1 wherein each of said eucalyptol, thymol, methyl salicylate and menthol is present in amount of at least about 5% by weight of said phenolic flavor.

3. An antiplaque oral composition according to claim 1 which is a toothpaste, gel dentifrice or tooth powder which comprises about 0.1–0.5% of triclosan and about 0.5–1.5% of phenolic flavor(s).

4. An antiplaque oral composition according to claim 1 which is a toothpaste or gel dentifrice and in which each of eucalyptol, thymol, methyl salicylate and menthol comprises no less than 10% of the phenolic flavor component thereof.

5. An antiplaque toothpaste or gel dentifrice according to claim 4 which comprises about 0.1–0.5% of triclosan, about 0.5–1.5% of a phenolic flavor for the toothpaste or gel dentifrice which includes at least about 0.05% of each of eucalyptol, thymol, methyl salicylate and menthol, about 10–40% of dental polishing agent, about 15–45% of humectant, about 0.5–8% of thickener, about 0.2–5% of surfactant and about 20–70% of water.

6. An antiplaque toothpaste according to claim 5 which comprises about 0.2–0.4% of triclosan, about 0.7–1.2% of phenolic flavor for the toothpaste which includes at least about 0.15% of each of eucalyptol, thymol, methyl salicylate and menthol, about 15–25% of finely divided silica dental polishing agent, about 20–40% of humectant, about 2–6% of gum and/or silica thickener(s) and about 0.5–3% of dental detergent surfactant.

7. An antiplaque oral composition according to claim 1 which is a mouthrinse or mouthwash which comprises about 0.01–0.2% of triclosan and about 0.02–1% of phenolic flavor.

8. An antiplaque oral composition according to claim 7, which is a mouthrinse or mouthwash which comprises about 0.01–0.1% of triclosan, and about 0.02–0.5% of said phenolic flavor.

9. An antiplaque mouthrinse or mouthwash according to claim 8 which comprises about 0.03–0.06% of triclosan, about 0.05–0.25% of phenolic flavor which includes at least about 10% thereof of each of eucalyptol, thymol, methyl salicylate and menthol, about 5–20% of ethanol, about 10–50% of humectant and up to about 85% of water.

10. An antiplaque mouthwash according to claim 9 which comprises about 0.03–0.06% of triclosan, about 0.05–0.25% of phenolic flavor which includes at least about 15% thereof of each of eucalyptol, thymol, methyl salicylate and menthol, about 0.05–1% of dental surfactant, about 1–20% of glycerol, about 1–20% of propylene glycol, about 1– 25% of sorbitol, and about 5–20% of propylene glycol, about 1–25% of sorbitol, and about 5–20% of ethanol and about 27.69–84.82% of water.

11. A process for treating teeth to inhibit plaque development on them which comprises applying to the teeth a plaque inhibiting amount of a composition of claim 1.

12. A process according to claim 11 wherein the composition applied to the teeth is a toothpaste or gel dentifrice which comprises about 0.1–0.5% of triclosan, about 0.5–1.5% of a phenolic flavor for the toothpaste or gel dentifrice which includes at least about 0.05% of each of eucalyptol, thymol, methyl salicylate and menthol, about 10–40% of dental polishing agent, about 15–45% of humectant, about 0.5–8% of thickener, about 0.2–5% of surfactant and about 20–70% of water, and such composition is applied to the teeth by brushing them with it at least once a day for at least seven consecutive days.

13. A process according to claim 12 wherein the composition applied to the teeth is a toothpaste which comprises about 0.2–0.4% of triclosan, about 0.7–1.2% of phenolic flavor for the toothpaste which includes at least about 0.15% of each of eucalyptol, thymol, methyl salicylate and menthol, about 20–40% of humectant, about 2–6% of gum and/or silica thickener(s) and about 0.5–3% of dental detergent surfactant and about 35–55% of water, and such toothpaste is applied to the teeth by brushing them with it at least twice a day for at least ten consecutive days.

14. A process according to claim 11 wherein the composition applied to the teeth is a mouthrinse or mouthwash which comprises about 0.01–0.1% of triclosan and about 0.02–0.5% of said phenolic flavor and such mouthrinse or mouthwash is applied to the teeth by rinsing the mouth containing such teeth with it at least once a day for at least four consecutive days.

15. A process according to claim 14 wherein the composition applied to the teeth is a mouthwash which comprises about 0.03–0.06% of triclosan, about 0.05–0.25% of phenolic flavor which includes at least about 15% thereof of each of eucalyptol, thymol, methyl salicylate and menthol, about 0.05–1% of a dental detergent surfactant, about 5–20% of ethanol, about 15–45% of humectant, and about 32.69–79.82% of water, and such mouthwash is applied to the teeth by washing the mouth with such mouthwash at least twice a day for at least seven consecutive days.

* * * * *